US012746133B2

(12) United States Patent
Johnson

(10) Patent No.: US 12,746,133 B2
(45) Date of Patent: Sep. 29, 2026

(54) ARTIFICIAL HAND

(71) Applicant: Phillip Johnson, Narrows, VA (US)

(72) Inventor: Phillip Johnson, Narrows, VA (US)

( * ) Notice: Subject to any disclaimer, the term of this patent is extended or adjusted under 35 U.S.C. 154(b) by 574 days.

(21) Appl. No.: 18/332,811

(22) Filed: Jun. 12, 2023

(65) Prior Publication Data

US 2024/0000586 A1 Jan. 4, 2024

Related U.S. Application Data

(60) Provisional application No. 63/367,288, filed on Jun. 29, 2022.

(51) Int. Cl.

| | |
|---|---|
| ***A61F 2/58*** | (2006.01) |
| ***A61F 2/68*** | (2006.01) |
| ***A61F 2/76*** | (2006.01) |
| ***A61F 2/78*** | (2006.01) |
| ***A61F 2/80*** | (2006.01) |

(52) U.S. Cl.

CPC ................ *A61F 2/588* (2013.01); *A61F 2/68* (2013.01); *A61F 2/76* (2013.01); *A61F 2/7812* (2013.01); *A61F 2/80* (2013.01); *A61F 2002/7818* (2013.01)

(58) Field of Classification Search

CPC .... A61F 2/588; A61F 2002/587; A61F 2/583; A61F 2/586

See application file for complete search history.

(56) References Cited

U.S. PATENT DOCUMENTS

| | | | | |
|---|---|---|---|---|
| 41,934 A | | 3/1864 | Monroe | |
| 1,153,532 A | | 9/1915 | Apgar | |
| 1,284,875 A | * | 11/1918 | Caron | A61F 2/588 623/65 |
| 1,365,692 A | * | 1/1921 | Henning | A61F 2/588 623/57 |
| 1,819,317 A | * | 8/1931 | Baehr | A61F 2/588 623/65 |
| 2,030,785 A | * | 2/1936 | Dorrance | A61F 2/54 623/65 |
| 2,696,011 A | | 12/1954 | Galdik | |
| 3,461,464 A | | 8/1969 | Lindgren | |
| 4,312,080 A | | 1/1982 | Staats | |
| 4,459,709 A | | 7/1984 | Leal et al. | |
| 4,872,879 A | | 10/1989 | Shamp | |
| 4,911,709 A | | 3/1990 | Marlow et al. | |
| 5,133,777 A | | 7/1992 | Arbogast et al. | |

(Continued)

OTHER PUBLICATIONS

D-Rev, ReMotion Knee, http://d-rev.org/projects/mobility/, retrieved Jun. 2, 2017 (4 pages).

(Continued)

*Primary Examiner* — Bruce E Snow
(74) *Attorney, Agent, or Firm* — Allan A. Fanucci Esq.

(57) ABSTRACT

An artificial hand, a kit of components for making the artificial hand and a method of making and installing the artificial hand on the arm stump of a person in need thereof. This artificial hand is made of relatively low-cost components and is fairly easy to assemble from a kit of such components. Additionally, the artificial hand can be relatively quickly and easily fit to the arm stump of a person in need thereof so that the person can wear and use the artificial hand immediately without excessive training or instructions.

20 Claims, 8 Drawing Sheets

(56) References Cited

U.S. PATENT DOCUMENTS

| | | | | |
|---|---|---|---|---|
| 5,228,164 | A | 7/1993 | Graf et al. | |
| 5,724,714 | A | 3/1998 | Love | |
| 5,888,231 | A | 3/1999 | Sandvig et al. | |
| 6,508,842 | B1 | 1/2003 | Caspers | |
| 6,793,682 | B1 | 9/2004 | Mantelmacher | |
| 7,153,327 | B1 | 12/2006 | Metzger | |
| 7,883,547 | B2 | 2/2011 | Mantelmacher | |
| 8,313,534 | B1 | 11/2012 | Chen et al. | |
| 10,376,390 | B1 | 8/2019 | Johnson | |
| 12,150,866 | B2 * | 11/2024 | Thompson, Jr. | A61F 2/76 |
| 2004/0153168 | A1 | 8/2004 | Childress et al. | |
| 2005/0015156 | A1 | 1/2005 | Hikichi | |
| 2005/0143839 | A1 | 6/2005 | Chen et al. | |
| 2006/0173554 | A1 | 8/2006 | Slemker et al. | |
| 2007/0055383 | A1 | 3/2007 | King | |
| 2008/0133019 | A1 | 6/2008 | Andrysek | |
| 2010/0114331 | A1 | 5/2010 | Mantelmacher | |
| 2010/0304205 | A1 | 12/2010 | Jo et al. | |
| 2010/0305698 | A1 | 12/2010 | Metzger et al. | |
| 2011/0009981 | A1 | 1/2011 | Okuda et al. | |
| 2014/0277584 | A1 | 9/2014 | Hurley et al. | |
| 2018/0161180 | A1 | 6/2018 | Arelekatti | |
| 2020/0297514 | A1 | 9/2020 | Prescott | |
| 2024/0000586 | A1 * | 1/2024 | Johnson | A61F 2/80 |

OTHER PUBLICATIONS

Williams, "Nonprofit Hope to Walk helping injured get back on their feet," The Roanoke Times, Mar. 26, 2016 (9 pages); http://www.roanoke.com/news/local/blacksburg/nonprofit-hope-to-walk-helping-injured-get-back-on-their/article_1ae3a731-e6bf-5bb6-aa93-09d2273d7bc2.html.

OConnor, "Johnson City man creates affordable prosthetics," News 5 WCYB, Sep. 30, 2015 (6 pages); http://www.wcyb.com/meet-the-term/kristi-oconnor/8196910).

Techform. Material Safety Data Sheet. Ossur, Jan. 2011. (in related U.S. Appl. No. 15/613,045, now U.S. Pat. No. 10,376,390.).

Össur, Modular Socket System-Direct Lamination, 2015. (in related U.S. Appl. No. 15/613,045, now U.S. Pat. No. 10,376,390.).

Össur, Össur Presents: Modular Socket System, YouTube video screen shot, Aug. 22, 2011. (in related U.S. Appl. No. 15/613,045, now U.S. Pat. No. 10,376,390.).

SPS PVA Bag, SPS Website; date verified by the wayback machine Mar. 7, 2016. (in related U.S. Appl. No. 15/613,045, now U.S. Pat. No. 10,376,390.).

U.S. Appl. No. 16/678,919, Non-Final Office Action, dated Dec. 8, 2020.

U.S. Appl. No. 16/678,919, Notice of Allowance, dated Apr. 15, 2022.

* cited by examiner

ARTIFICIAL HAND

CROSS-REFERENCE TO RELATED APPLICATIONS

This application claims the benefit of U.S. provisional application No. 63/367,288 filed Jun. 29, 2022, the entire content of which is expressly incorporated herein by reference thereto.

FIELD OF THE INVENTION

The invention relates a prosthetic device in the form of an artificial hand, a kit of components for making the artificial hand and a method of making and installing the artificial hand on the arm stump of a person in need thereof. In particular, the invention provides an artificial hand that is of relatively low cost and easy to assemble from a kit of components. Additionally, the artificial hand can be relatively quickly and easily fit to the arm stump of a person in need thereof so that the person can wear and use the artificial hand immediately without excessive training or instructions.

DESCRIPTION OF THE RELATED ART

Throughout history, humans have lost limbs as a result of accidents, military combat, illnesses, and hereditary defects. In the United States, approximately 2 million people have had amputation of an arm or leg. As medical science improved, various prosthetic limbs have become available. These prosthetics are artificial devices that replace missing body parts, and have been manufactured out of metals, plastics, wood, leather, carbon, polycarbonates, resins, and laminates. Artificial hands, in particular, have been made in a complicated and expensive fashion utilizing electronics and sophisticated parts to try to mimic the operation of a hand. This causes the cost of such items to be prohibitive for people in less affluent countries. Additionally, the use and maintenance of such prosthetics requires specialized training and experience. To the knowledge of the inventor, there are no low-cost artificial hand prosthetics that can function appropriately to assist disabled persons and enable them to use the hand to conduct various work activities. The present invention now satisfies this need.

SUMMARY OF THE INVENTION

The invention now provides an artificial hand for a person in need thereof comprising first and second palm members, each containing at least one finger component, with the palm members connected together for rotation between a first, closed position wherein the finger components of the palm members are interspersed together and a second, open position wherein the finger components are spaced apart to allow grasping of an object. The artificial hand also includes an alignment mechanism associated with the first and second palm members to guide rotation between the first and second positions, wherein the alignment mechanism comprises a tab member located on the first palm member and spaced sidewalls on the second palm member defining a slot therebetween, wherein the slot is configured and dimensioned to receive an upper portion of the tab member therein to facilitate rotation between the first and second positions.

To facilitate rotation between the first and second positions, a fastener is provided for connecting the first and second palm members together, wherein the fastener passes through the side walls and slot of the second palm member and through a lower portion of the tab member of the first palm member. Also provided is a biasing member operatively associated with the first and second palm members. The biasing member is configured and arranged for urging the palm members towards the first position. The biasing member is further configured and dimensioned to be stretched or elongated to allow the palm members and their respective finger components to move to the second, open position to receive an object and to secure the object between the finger components as the biasing member attempts to contract from being stretched or elongated. A force is provided to the palm members to overcome the force of the biasing member to move the palm members to the second, open position by stretching or elongating the biasing member. Thus, when the force utilized to stretch or elongate the biasing member is removed, the biasing member attempts to return to its original configuration and shape thus urging the palm members to move toward the first position. This enables enable the finger components to grasp the object or to secure the object between them.

The at least one finger component of the first palm member advantageously includes one finger component a portion which is elongated and arcuate. Also, the at least one finger component of the second palm member includes at least two finger components, each having a portion of which is elongated and arcuate. The arcuate portions are arranged on the respective finger components to face each other and define an opening therebetween when the palm members and finger components are in the second, open position. Preferably, the one finger component of the first palm member is interdigitated between the two finger components of the second palm member. If desired, a stop member can be provided for the first, closed position, wherein the tab member of the first palm member includes a wall that is configured and dimensioned to contact a rear wall of the slot of the second palm member such that engagement and contact of these walls with each other acts as the stop member.

For a light weight construction, the palm members are made of plastic with the fastener preferably being a horizontal bolt that passes through the side walls and slot of the second palm component and through the lower portion of the tab member of the first palm member with the bolt secured by a washer and nut. The first and second palm members preferably include a groove or recess on an outer portion thereof to receive a portion of the biasing member therein, and the biasing member preferably is a flexible, solid, natural rubber rod, cord or strap.

For improved gripping, the finger components of the first and second palm members may include pad members respectively located on the portions that are arcuate, distal portions of the finger components, or on both the arcuate portions and the distal portions of the finger components. These pad members are made of a compressible rubber or polyurethane material which provide a better grip on the objects to be held.

A base member is advantageously provided to support the palm members. This base member includes a first cavity at one end and a second cavity at the opposite end, wherein the first palm member includes a mounting extension extending below the tab member for placement into and securement to the first cavity of the base member. This fixes the position of the first palm member such that only the second palm member moves to the second position.

A pylon is advantageously provided for connection to the base member. The pylon has a first end which is received in and secured to the second cavity of the base member. This pylon preferably comprises a wooden dowel within a plastic tube. A coupling member is typically provided to facilitate application of the artificial hand to the arm stump of a person in need thereof. This coupling member has a cylindrical body, a cavity for receiving and securing thereto a second end of the pylon, and a closed base configured for attachment to the person's arm stump.

To facilitate opening of the finger components by overcoming the force of the biasing member, the artificial hand further comprises a grasping member operatively associated with the second palm member for moving that palm member towards or to the second, open position. Preferably, the grasping member comprises a pull cord, a first end of which is secured to the second palm member and a second end of which is associated with the base member. Advantageously, the second palm member or its respective finger component along with the base member each include a guide hole, wherein the pull cord passes through each guide hole, the first end includes a knot to prevent the pull cord from passing back through the guide hole of the second palm member, and the second end passes through the guide hole of the base member for grasping by the opposite hand of the user. The second end of the pull cord can be provided with a loop if desired to assist in pulling the cord to open the artificial hand.

The invention also relates to a kit for preparing an artificial hand for a person having a missing hand and a remaining arm stump, the kit having a plurality of components as described herein. The components of the kit are of low cost and assembly of the artificial hand is straightforward, such that the artificial hand of the invention can be made available to many persons in need thereof and in particular to those in underdeveloped or poorer countries.

Generally, the kit includes the palm members, the fastener, the biasing member, the base member, the pylon and the coupling member as described herein. For installation or application of the hand to a person's arm stump, the kit can also include a flexible sheath configured and adapted to fit on the person's arm stump; a casting sock of a fabric containing a water activated settable material that, after activation, is adapted to fit over the flexible sheath; and casting tape of a fabric containing a water activated settable material and provided in one or more lengths that, after activation, are capable of attaching the coupling member to the person's arm stump while also covering the flexible sheath. If desired, these installation components can instead be provided in a separate kit.

The invention also relates to a method for preparing artificial hand from a kit of the components for a person having a missing hand and a remaining arm stump, wherein the method comprises assembling the artificial hand by connecting the palm members with the fastener; placing the biasing member about the palm members; and inserting the first palm member into the base member. When a pull cord is to be included, the method includes placing the pull cord through the guide holes of the first palm member and base member so that the person can open the artificial hand by using his or her anatomical hand to pull on the pull cord. If desired, the free end of the pull cord can be provided with a loop to assist in grasping engagement.

And to install the prepared artificial hand on a person in need thereof, the method further comprises the additional steps of applying a fabric or cloth sock on the person's arm stump; applying a separator bag over the sock on the person's arm stump; applying the flexible sheath upon the sock and bag on the person's arm stump; activating the casting sock by immersion in water and applying the activated casting sock to the flexible sheath; providing the coupling member beneath the casting sock and separator bag with a base surface of the coupling member contacting the casting sock and separator bag; activating the casting tape by immersion in water; attaching the coupling member to the person's stump covered by the casting sock by wrapping the activated casting tape around the coupling member while also covering the flexible sheath; cutting the pylon to an appropriate length so that the artificial hand is positioned to match that of the anatomical hand of the person; and attaching one end of the pylon to the cavity of the coupling member and the other end to the artificial hand.

BRIEF DESCRIPTION OF THE DRAWINGS

Preferred features of the invention are now provided upon review of the appended drawing figures, wherein.

DETAILED DESCRIPTION OF THE INVENTION

Figure 1:
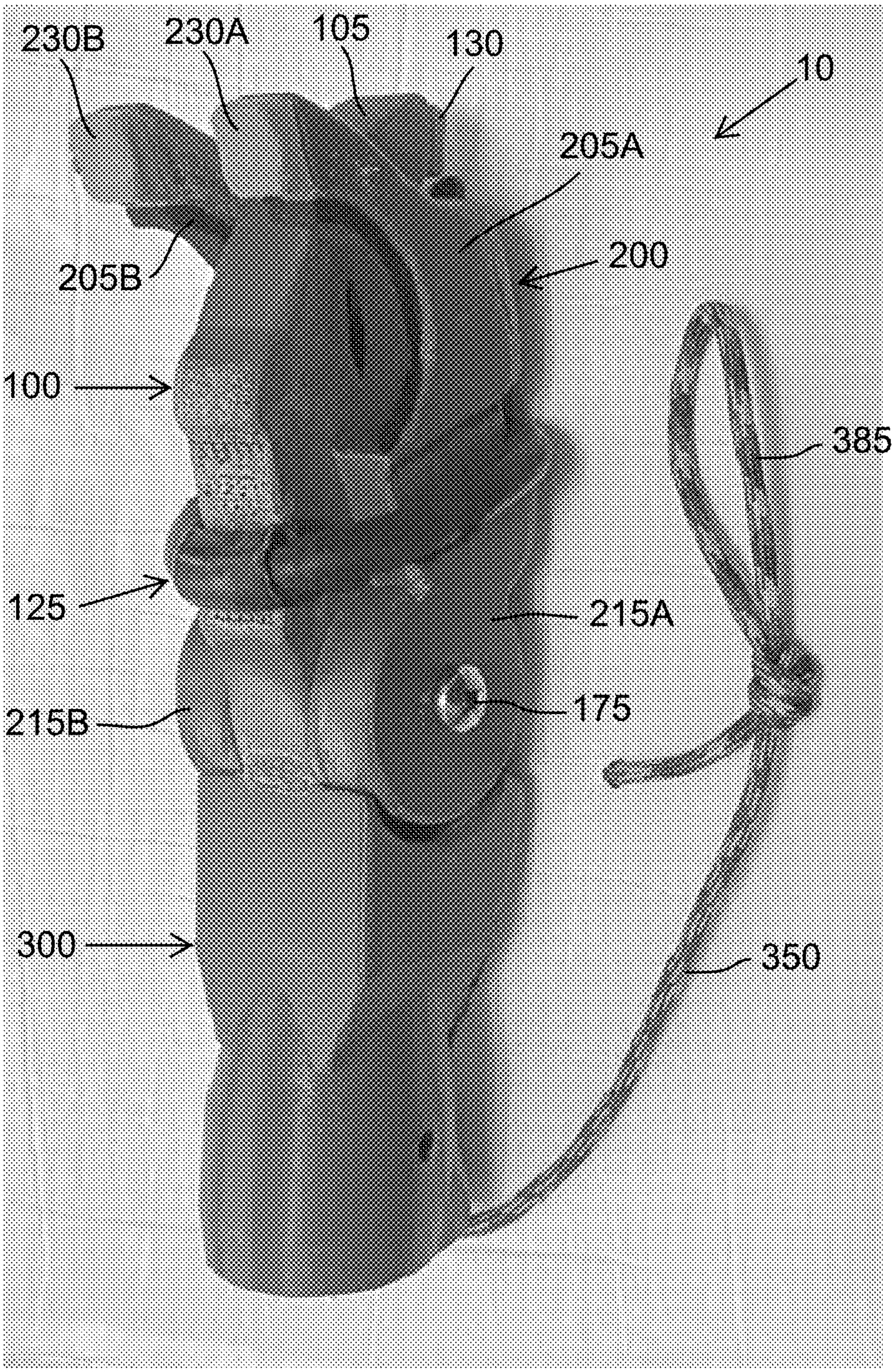
FIG. 1 depicts the main components of an artificial hand according to the invention with the palm member and finger components in the first, closed position with the biasing member holding the palm member in that position.

A preferred embodiment of the artificial hand of the present invention is now described. FIG. 1 depicts an artificial hand 10 according to the invention. The hand includes a number of main components including a first palm member 100, a biasing member 125, a second palm member 200, and a base member 300. The first palm member has one elongated arcuate finger 105 while the second palm member 200 has two elongated arcuate fingers 205A, 205B. The biasing member 150 is typically a flexible and stretchable rubber O-ring that is configured to have a smaller diameter than when placed about the palm members such that the biasing member tries to return to its original diameter to thus hold the palm members in the closed position. In that position, the finger components of the two palm members are interspersed or interdigitated together as shown.

The palm members 100, 200 include lower portions that are connected together by a bolt 175 which is secured using a conventional lock washer and nut. Palm member 200 includes lower sidewall portions 215A, 215B that form a slot therebetween in which a lower portion of the tab member of the first palm member 100 can move to place the palm members in the closed position or in the open position. Pull cord 350 is provided to assist in moving the second palm member to the open position.

Figure 2:
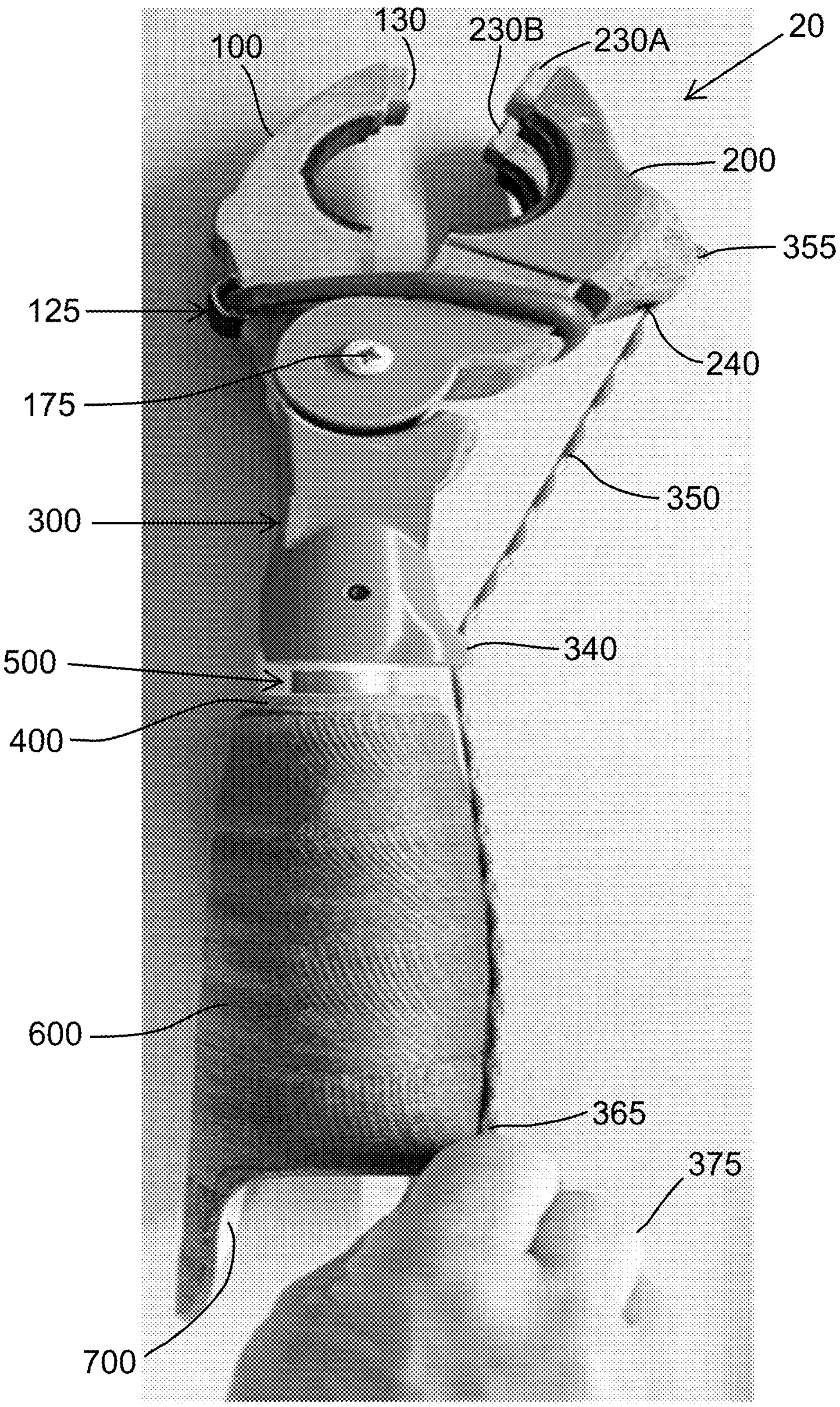
FIG. 2 depicts the artificial hand of FIG. 1 with the biasing member stretched such that the palm members are in the second, open position for grasping of an object.

FIG. 2 depicts the artificial hand of FIG. 1 with the biasing member 125 stretched such that the palm members are in the open position wherein the finger components of the two palm members are spaced apart to allow grasping of an object. In a preferred embodiment, palm member 100 is fixed in position whereas palm member 200 can be moved between the closed and open positions. The artificial hand 20 of this FIG. 2 is shown connected to a coupling member 400 by the use of pylon 500. Also shown is casting tape 600 which is applied over coupling member 400 and a flexible plastic sleeve 700 that is initially provided over the patient's arm stump.

Artificial hand 20 is typically applied to the arm stump of a patient that has compete use of his or her other hand. Therefore, the patient can simply grasp the palm member 200 and pull it away from engagement with palm member 100 to provide the open position for grasping of an object. To facilitate this operation, however, a grasping member operatively associated with the palm member 200 is provided for moving that palm member towards or to the open position. This grasping member preferably comprises a pull cord 350 that advantageously is secured to guide holes 240, 340 respectively located in palm member 200 and base member 300 as shown. One end of the pull cord 355 can be provided with a knot so that that end of the cord will not be able to pass through guide hole 240 in palm member 200. The pull cord then extends through guide hole 340 in base member 300 and extends towards the person's arm. The free opposite end 365 of the pull cord can be grasped by the other hand 375 of the person. Pulling on pull cord 350 causes palm member 200 to be moved toward or into the open position so that the palm members can receive and then be secured about an object, such as a broom or other tool for conducting activities that would not otherwise be possible without the presence of the artificial hand. Hand 375 can grasp the free end of the pull cord whether it is straight or provided with a loop 385 as shown in FIG. 1.

The finger components 105, 205A, 205B can grasp an object by release of the pull cord so that the biasing member 125 attempts to force the second palm member 200 to return to the closed position. As can be appreciated, if the object to be grasped is larger than the opening defined by the arcuate shapes of the finger components of the respective palm members, a secure grip about the object is achieved. It is also possible for the artificial hand to grasp a flat or rectangular object between the ends of the finger components of the palm members. To assist in the securement of that type object, a compressible pad member 130 is provided on the end of finger component 105 of palm member 100, while similar compressible pad members 230 and 235 are provided on the finger components of the second palm member. These pad members are typically made of a compressible rubber or polyurethane material.

Figure 3:
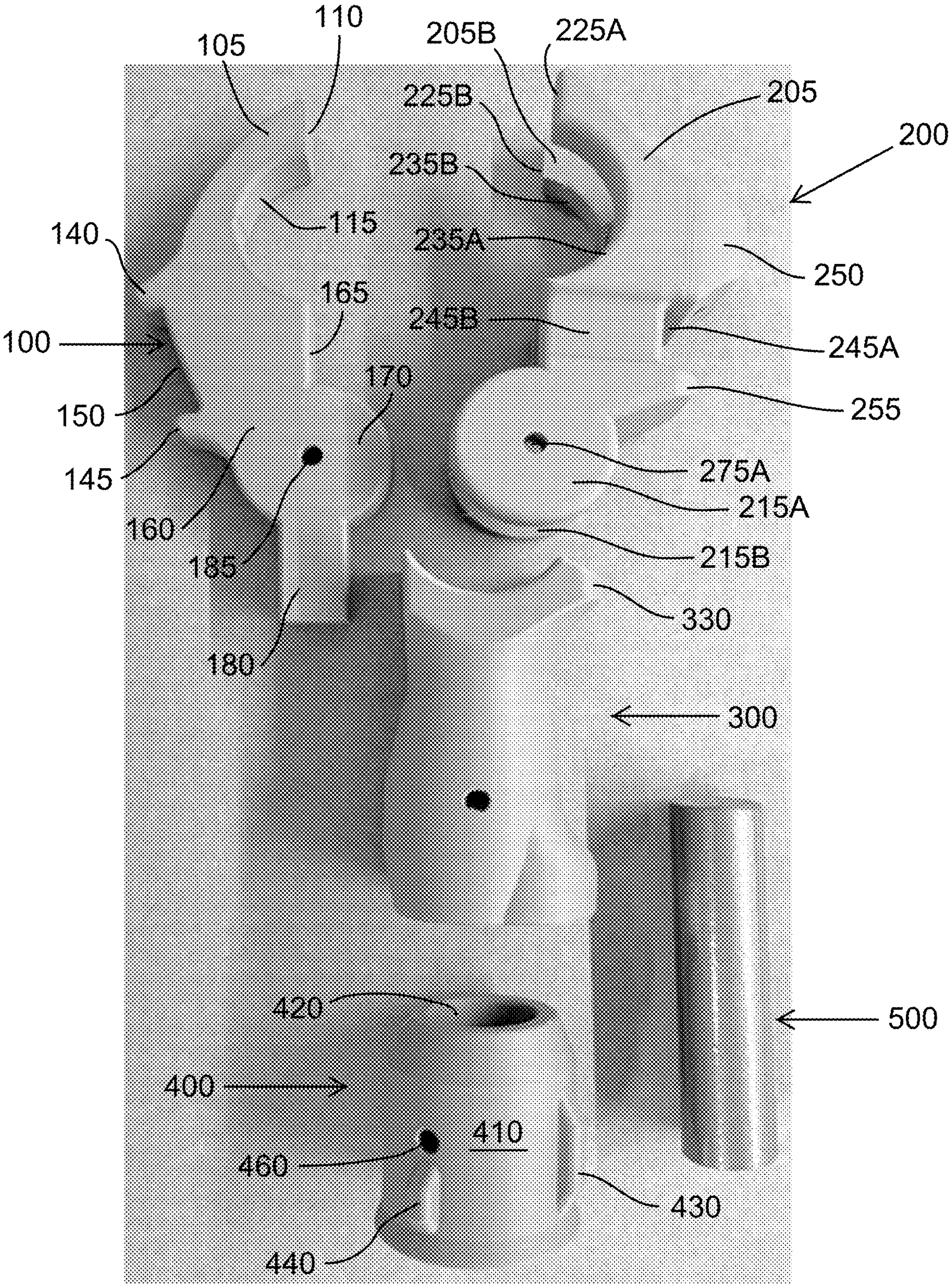
FIG. 3 shows the main components of the artificial hand of FIG. 1 in an exploded and separated arrangement.
Figure 4:
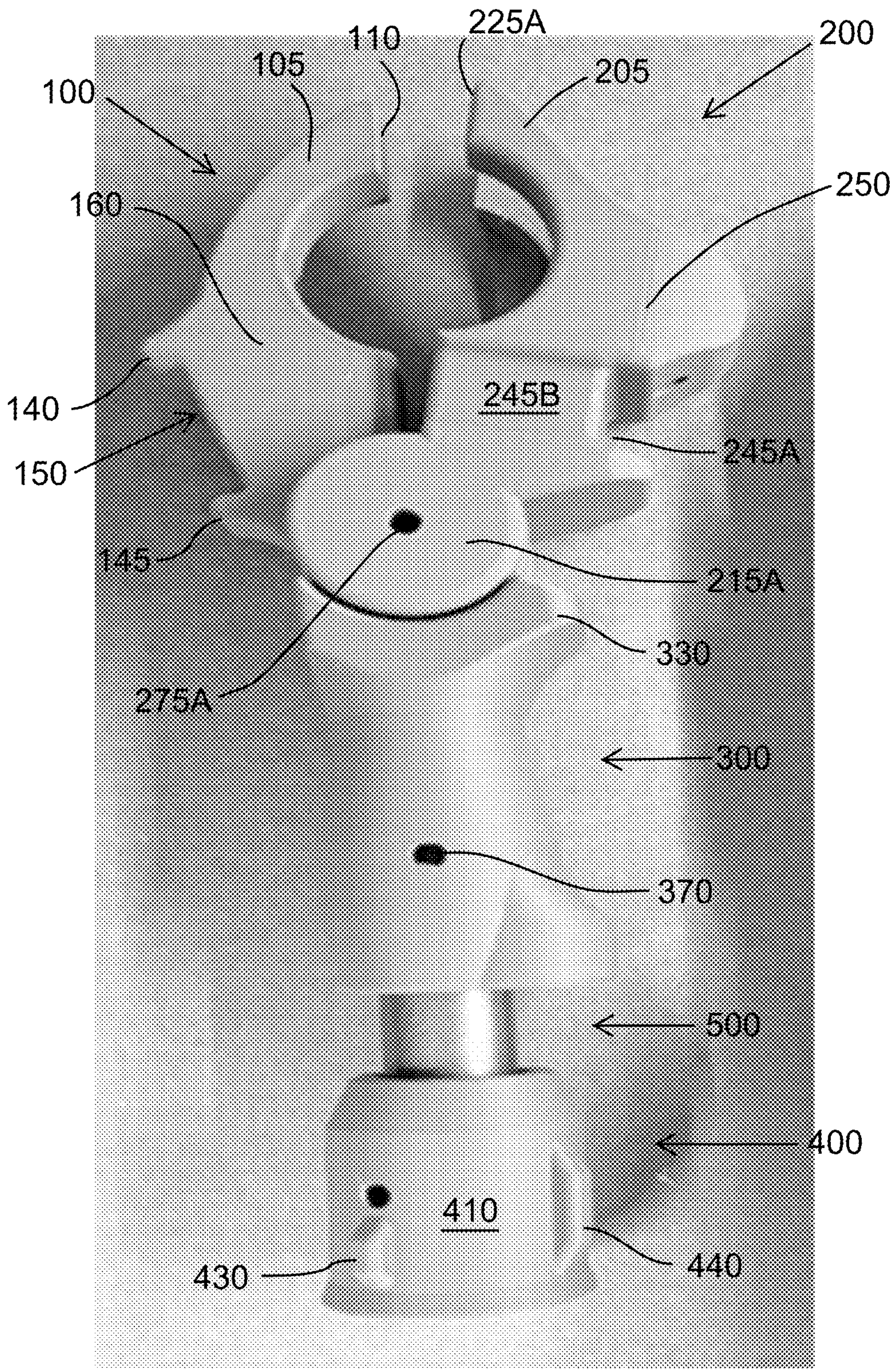
FIG. 4 shows the artificial hand components of FIG. 3 in a partially assembled position.

Further details of the components of the artificial hand of the invention are best shown in FIGS. 3 to 12. FIG. 3 shows the main components of the artificial hand of FIG. 1 in an exploded and separated arrangement, while FIG. 4 shows the artificial hand components of FIG. 3 in a partially assembled position.

Figure 6:
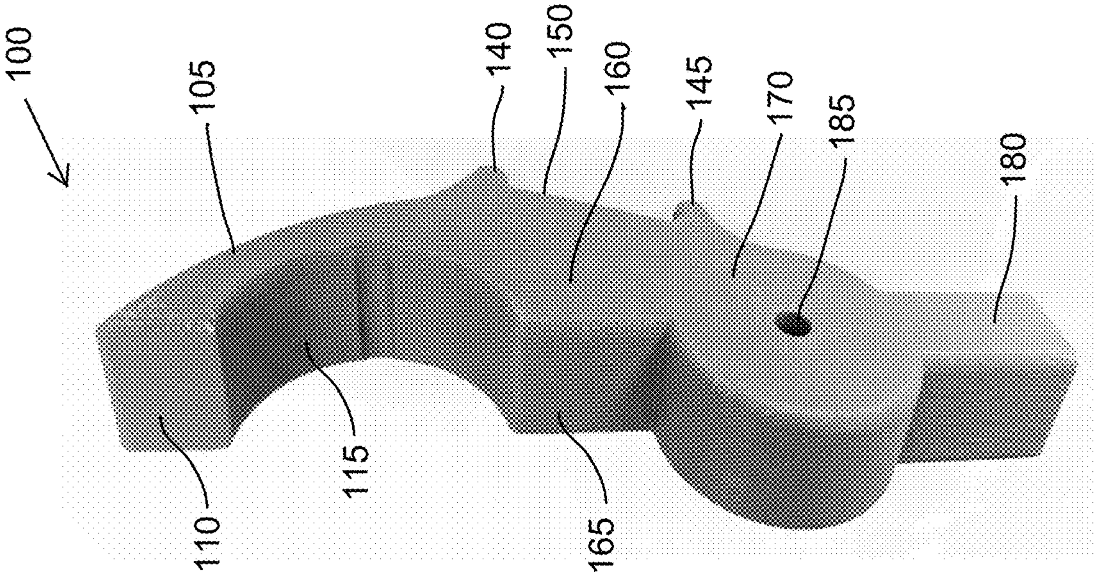
FIG. 6 is a perspective view of inner side of the first palm member of the artificial hand of the invention.
Figure 5:
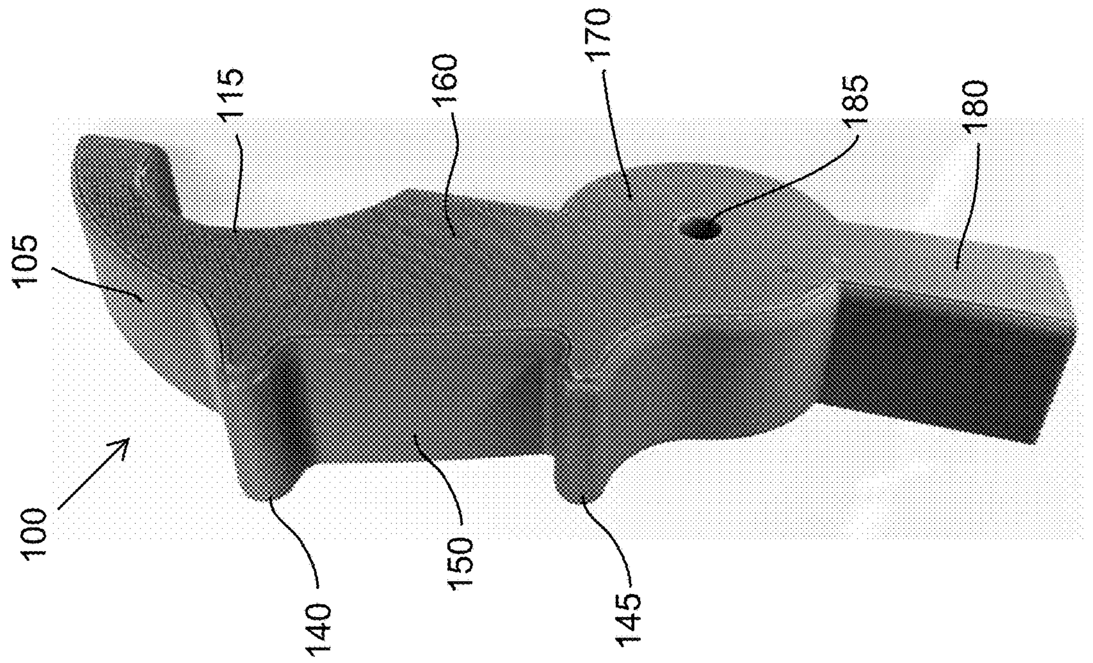
FIG. 5 is a perspective view of the outer side of the first palm member of the artificial hand of the invention.

The details of palm member 100 are best shown in FIGS. 5-6. Palm member 100 includes finger component 105, the end of which 110 is shown prior to being provided with optional pad member 130, and the inner side of which includes arcuate portion 115. To help retain biasing member 125 in the correct engagement position, the outer surface of palm member 100 is provided with two ridges 140, 145 which define a recess 150 therebetween which captures the biasing member. The ridges prevent movement of the biasing member to higher or lower positions on palm member 100. Palm member 100 also includes a tab member 160, having an inner wall 165 and lower portion 170. Lower portion 170 of tab member 160 has a disc like shape and includes a through hole 185. Palm member 100 also includes a mounting extension 170 beneath the tab member 160 for engagement with the base member 300.

Figure 8:
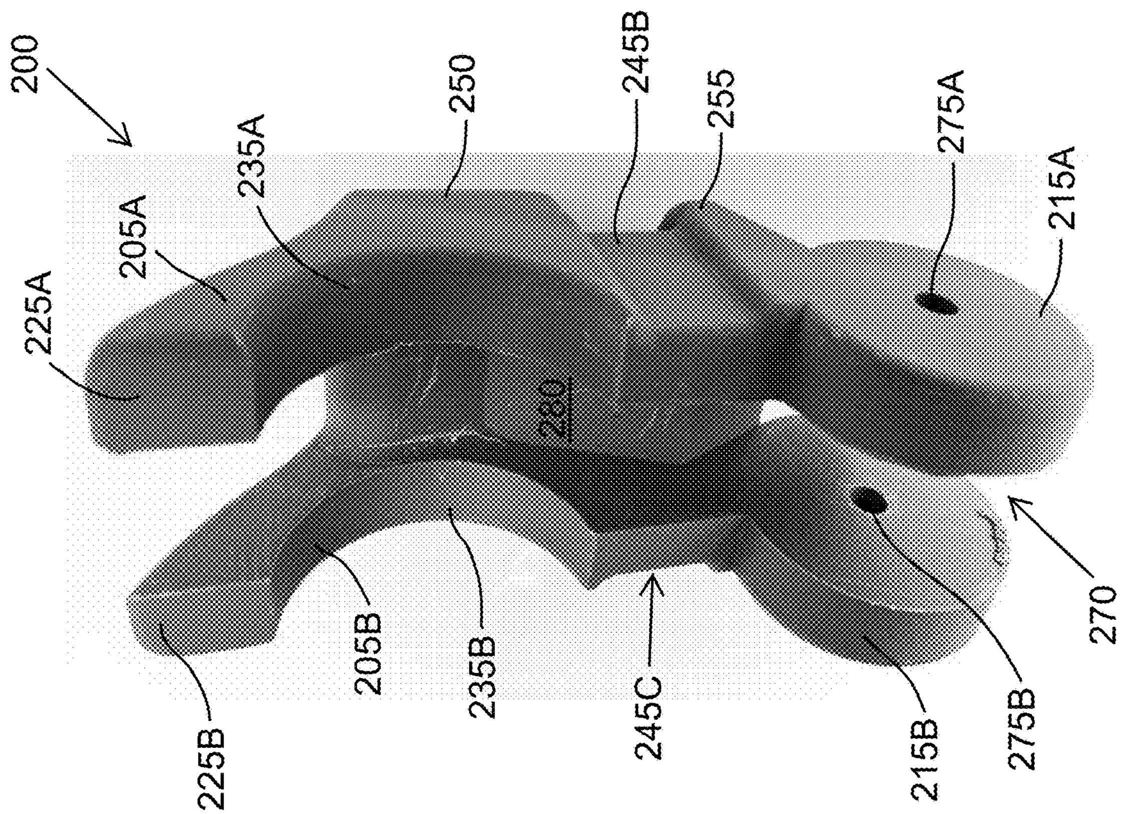
FIG. 8 is a perspective view of inner side of the second palm member of the artificial hand of the invention.
Figure 7:
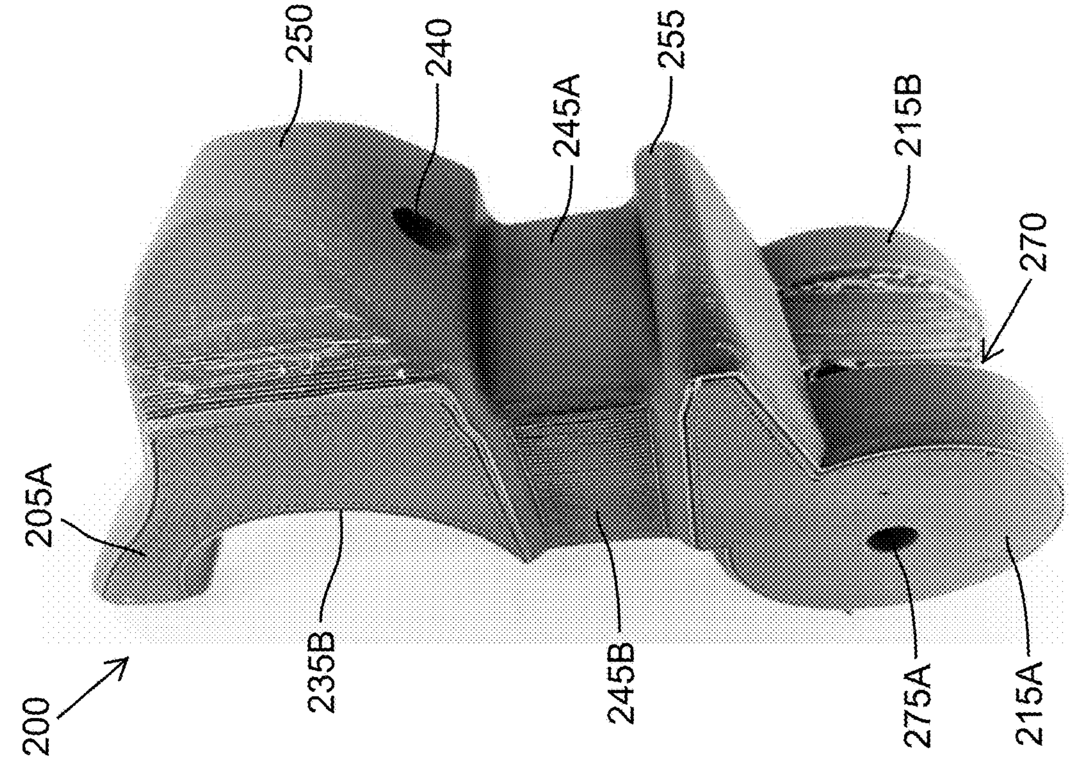
FIG. 7 is a perspective view of the outer side of the second palm member of the artificial hand of the invention.

The details of palm member 200 are best shown in FIGS. 7-8. Palm member 200 includes two finger components 205A, 205B, the ends of which 225A, 225B are shown prior to being provided with optional pad members 230A, 230B, and the inner side of which includes arcuate portions 235A, 235B. To help retain biasing member 125 in the correct engagement position, the outer surface of palm member 200 is provided with two ridges 250, 255 which define a recess 245A therebetween. The recess provided by recess 245A continues on sides of palm member 200 to form additional recesses 245B, 245C that help capture the biasing member. These additional recesses 245B, 245C are provided because those portions of palm member 200 are positioned outside of the tab member 165 of palm member 100. With this construction, the various ridges and recesses of the two palm members prevent movement of the biasing member to higher or lower positions where it would not operate effectively. Palm member 200 also includes disc members 215A, 215B which together form slot 270 therebetween which receives therein tab member 165 including its disc shaped lower portion 170. This arrangement acts as an alignment member to guide rotation of the second palm member between the first and second positions. Disc members 215A, 215B respectively include through holes 275A, 275B. Fastener 175 passes through holes 275A, 275B and slot 270 of palm member 200 and hole 185 of palm member 100 to secure the palm members together. When connected in this manner, palm member 200 is capable of moving between the closed position and the open position by rotation of disc members 215A, 215B with respect to tab member 170. Also, the closed position is achieved when inner wall 280 of slot 270 of palm member 200 contacts inner wall 165 of tab member 160 of palm member 100 with these walls cooperating to function as a stop member against further closing movement of palm member 200. This is best seen with the artificial hand in the closed position as shown in FIG. 1. As the biasing member is stretched or elongated to allow the palm members and their respective finger components to move to the open position to receive an object, release of the force which moved the second palm component to the open position secures the object between the finger components as the biasing member contracts and tries to return to its original shape.

Figure 9:
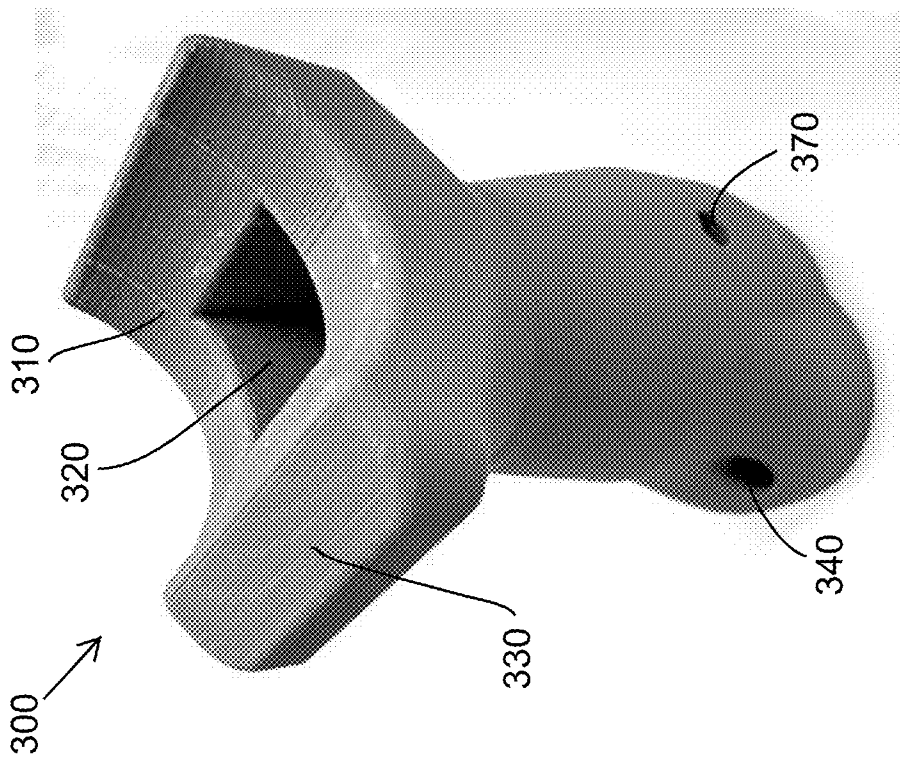
FIG. 9 is a top perspective view of the base member of the artificial hand of the invention.
Figure 10:
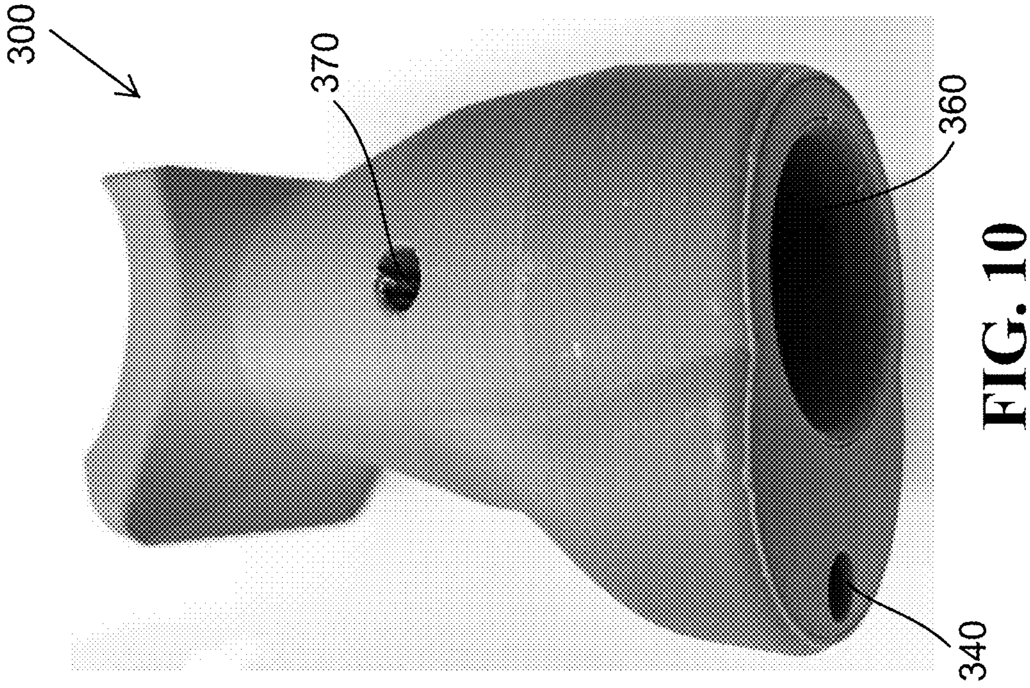
FIG. 10 is a bottom perspective view of the base member of the artificial hand of the invention.

The details of base member 300 are best shown in FIGS. 9 and 10. Base member 300 includes an arcuate upper surface 310 to support the disc shaped portion of tab 170 of palm member 100 and disc members 215A, 215B of palm member 200. In a central area of this arcuate surface, a first cavity 320 is provided. This cavity 320 is configured and dimensioned to receive the mounting extension 180 of palm member 100. The mounting extension preferably has a square cross section and the cavity is configured to receive that shape. This prevents rotation of the palm members during use. Of course, other configurations such as round, oval, triangular, rectangular, etc. can also be used. Advantageously, the mounting extension 180 can be secured to the cavity 320 by a suitable adhesive so that there is no concern of it being removed when the artificial hand is trying to exert pulling forces on an object. Alternatively, the mounting extension can be secured in the cavity using screws or other fastener arrangements.

When so mounted, the base member cooperates with palm member 200 to provide a stop member that prevents movement of palm member 200 beyond a fully open position. This stop member is formed when a lower portion of ridge 255 engages wall member 330 of base member 300. Thus, palm member 200 cannot be rotated beyond the point where ridge 255 contacts wall member 330. Base member 300 also includes guide hole 340 which is configured to receive pull cord 350 as shown in FIG. 2. This guide hole 340 enables the pull cord 350 to remain close to the person for easy engagement when it is desired to move palm member 200 to the open position. Of course, pull cord 350 has a length sufficient to allow a knot at the forward end and extending at least to the person's arm stump. Finally, base member 320 also includes a cavity 360 in the lower surface and through hole 370. The cavity and through hole facilitate the connection of the artificial hand to other components necessary for connection of the artificial hand to the arm stump of a person in need thereof.

Figure 11:
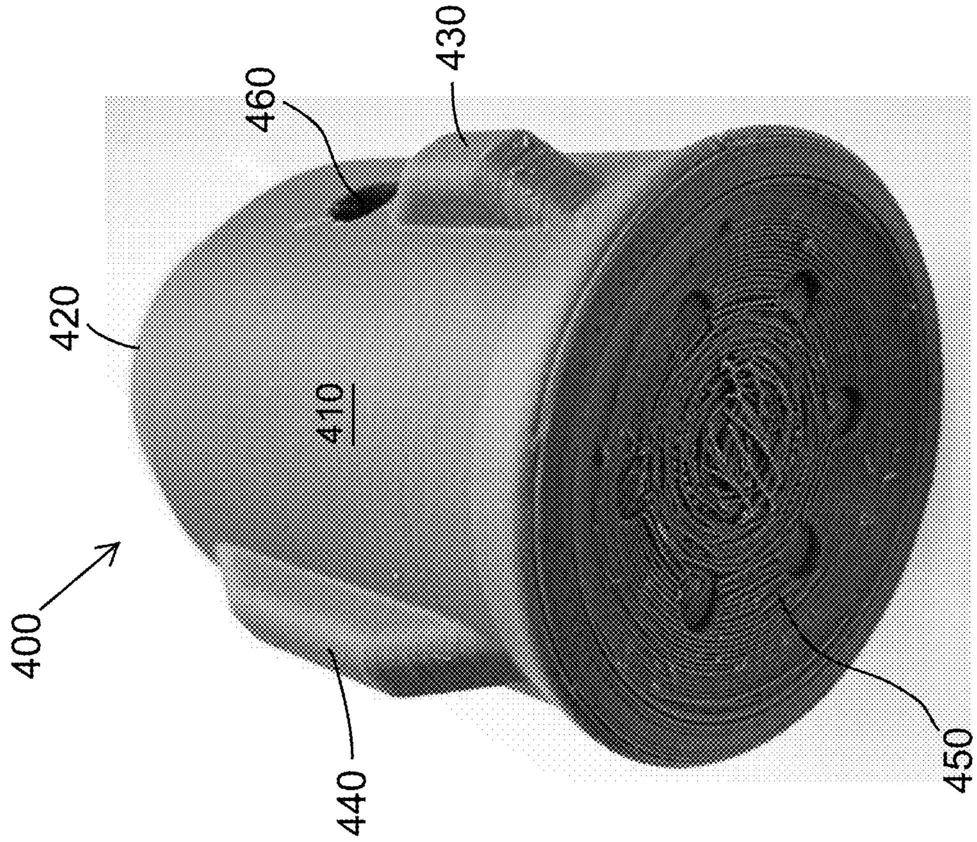
FIG. 11 is a bottom perspective view of the coupling member of the artificial hand of the invention.

To make such a connection, a coupling member 300 is provided. This coupling member 400, which is best shown in FIGS. 3, 4 and 11, includes a generally cylindrical body member 410 having a centrally located cavity 420 extending to an upper surface thereof. The body also includes rib members 430, 440. The bottom of the coupling member includes a closed base 450 having a slightly arcuate surface which is configured for engaging the person's arm stump. Also included is a through hole 460 in the sidewall of the body 410.

Figure 12:
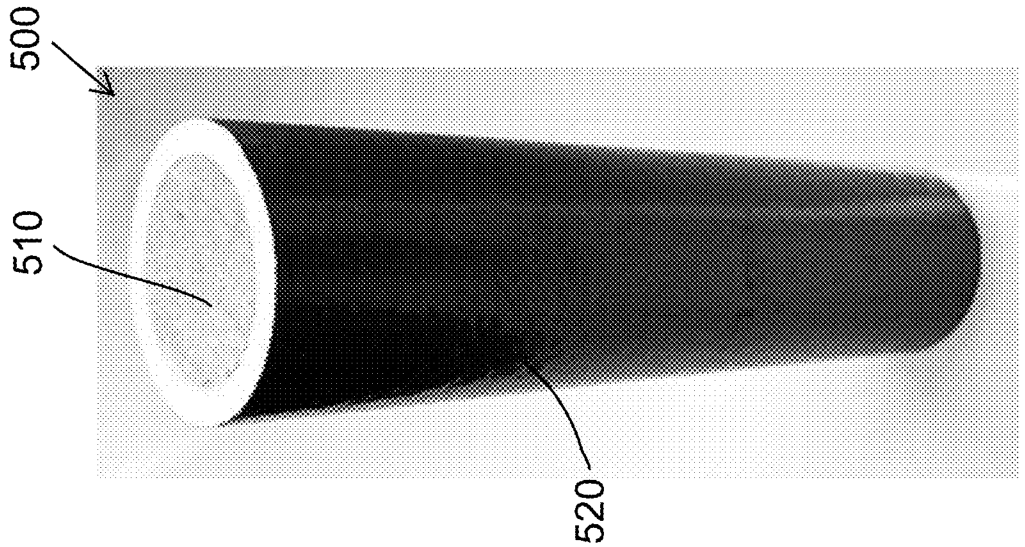
FIG. 12 is a top perspective view of the pylon that connects the base member to the coupling member of the artificial hand of the invention.

The coupling member 400 is connected to the base member 300 utilizing a pylon 500. Pylon 500 can be made of many different materials, including metal, wood, rigid plastic or other materials having similar structural features. For lowest cost, a wood dowel can be used. A better arrangement for pylon 500 comprises a wooden dowel 510 encased within a plastic tube 520, as shown in FIG. 12. If desired, the dowel 510 can be adjusted to be longer than the plastic tube so that the dowel 510 protrudes from one or both open ends of the plastic tube 520. The length of the pylon can then be adjusted by a knife, a blade, a saw, or other cutting tool that is readily available to the length needed to properly size the length of the connection of the base member to the coupling member. One end of the pylon 500 extends into cavity 420 of the coupling member and the other end extends into cavity 360 of base member 320. The pylon is secured into those members either using a strong adhesive that is placed in the cavities or on the outer end portions of the dowel, or by the use of screws or bolts that extend through those members and into the pylon. Guide holes 370 and 460 are provided to facilitate the use of screws or bolting. For the latter, holes can be drilled through the pylon using the guide holes 370 and 460 after the pylon is inserted into the base and coupling members. This is easily achieved by simply inserting a drill into the guide holes of the base member and coupling member. After the pylon is provided with holes in alignment with holes 370 and 460, suitable bolts can be passed therethrough. The bolts secure these components together by engaging a nut and lock washer assembly.

To provide a lightweight device with sufficient strength, each of the palm, base and coupling members are made of a plastic material, with polylactic acid (PLA) being preferred with the components being 3D printed. Of course, other high strength plastic materials that can be molded to the desired shapes can also be used. Examples of such materials include ULTEM (polyetherimide), PEEK (polyether ether ketone), PPS (polyphenylene sulfide) and LCP (liquid crystal polymer). A skilled artisan can select the optimum plastic material for these parts from these or other plastic materials.

Each of the plurality of components is low-cost and is made from low-cost materials and/or manufactured at low-cost. Low-cost may refer to materials able to be purchased inexpensively from generally available materials that can be tailored or conformed to the person in need using readily available and simple manufacturing tools or machines. Thus, the kit allows the assembly and attachment of the artificial hand at relatively low cost in just about any location. It also is particularly useful for persons in low income or poverty areas. The artificial hand prepared from the kit is substantially less expensive compared to prostheses currently in the market which may cost between $5,000 and $50,000 or more. The kit generally costs less than $100, and the artificial hand prepared from the kit by a health care professional would cost than less $200. Therefore, the artificial hand prepared from the kit costs much less than an average-cost hand prosthesis in the current market. The artificial hand is also simple to assemble from the kit such that it can be assembled by a layperson, e.g., a family member or a friend, after reading the preparation steps and instruction details provided in the kit as described herein. The kits can also be provided at no cost by being donated to certain impoverished or war-torn areas. In those situations, the artificial hand would be provided at an even lower cost or even at no cost to persons in need that would otherwise not be able to obtain one.

For attaching the artificial hand to the person, a sock is first placed on the person's arm stump. The sock directly touches the person's arm stump and provides some buffer between the skin and the components to be attached, just like a sock worn on a foot provides cushioning to shoes which are worn on the foot. The sock is typically a fabric sock that may made of cotton, wool, nylon, acrylic, polyester, olefins (such as polypropylene), spandex, linen, or any combination thereof. The fabric sock may also be made of other materials that provide comfort to the person's arm stump. The sock has an open end and a closed end and is slipped onto the person's arm stump with the closed end positioned at the end of the stump. The sock is configured to be at least as long as the flexible shield that is to be later applied.

To protect the person's skin from contact with the casting sock, a separator bag is applied to cover the sock and the person's stump to provide a barrier to the additional casting materials that are to be added. The separator bag has a size or volume sufficient to cover the area on the sock where the subsequently applied casting sock will be applied. The separator bag preferably has a longitudinal length that is longer than that of the casting sock to be later applied. The separator bag is preferably made of a waterproof material, such as polyurethane, polyamide, polyester, polyolefin (e.g., polyethylene and polypropylene), fluoropolymer, or any combination thereof. Other materials and combinations having similar characteristics may also be used. The separator bag prevents the settable material of the casting sock and water from soaking the sock or contacting the person's arm stump. The separator bag is conveniently a plastic tubular bag.

Alternatively, a plastic film such as Saran® wrap can be used instead of the bag.

The artificial hand as well as a kit for assembling the hand will require additional components for connection of the artificial hand to the arm stump of a person in need thereof. These additional components include a flexible sheath or casting sock 700 as shown in FIG. 2 which is configured and adapted to fit over the fabric sock and separator bag or plastic film on the person's arm stump. The casting sock is made of a reinforced settable material that is activated by placement in water and then fitted onto the person's stump which is protected by the fabric sock and plastic bag or film. The casting sock is then allowed to set or cure to a solid shape. Next, the coupling member base 450 is then placed adjacent the cured casting sock, and is attached thereto by wrapping with a casting tape that is activatable by water is moistened and wrapped around both components. The resulting cured structure forms an enclosure 600 as shown in FIG. 2 which secures the coupling member to the flexible sheath.

The cured casting sock can also be provided with a tape preferably made of rubber or an elastomeric material or of another material that has similar flexibility characteristics. A flexible synthetic stocking or expandable tube can also be used. This protects the casting tape from water or other environmental conditions.

The casting tape may comprise a fabric containing a water activated settable material. The fabric may be made of the same material as the casting sock or of a different fabric material that is sufficiently porous to hold the settable material. The casting sock is preferably made of polyester. The water activated settable material may comprise resin such as polyurethane resin, polyester resin, polyisocyanate resin, epoxy resin, plaster, or the like. The water activated settable material is preferably polyurethane resin. The casting sock is activated by providing water to it. In one embodiment, the casting sock is simply immersed in water for activation. Once activated, the casting sock is applied to wrap over the coupling member and at least part or all of the flexible sheath, the separator bag, and the sock when those components are positioned on the person's arm stump. When the casting sock is provided as a roll, after activation, the tape is unrolled and wrapped around the other components to attach them together to the person's arm stump. The water activated settable material may cure within minutes once activated which hardens the casting sock. The water activated settable material may also be considered as a water-curable material. The casting sock may be a casting sock manufactured by STS.

Table 1 is an illustrative flow chart for the method of preparing the artificial hand of the invention from a kit of components

TABLE 1

Assembling an artificial hand from a kit of components therefore

| Number | Step Details |
| --- | --- |
| 1 | Place lower portion 170 of tab member 165 of palm member 100 into slot 270 of palm member 200 with holes 185, 275A and 275B in alignment |
| 2 | Push bolt 175 through holes 185, 275A and 275B until bolt head contacts disc 215A and the threaded end of the bolt extends past disc member 215B |
| 3 | Apply nut and lock washer onto the threaded end of bolt 175 to secure palm members 100 and 200 together |
| 4 | Apply biasing member 125 into recesses 150, 245A, 245B, and 245C |
| 5 | Apply adhesive to extension member 180 of palm member 100 or into cavity 320 of base member 300 |
| 6 | Insert extension member 180 of palm member 100 into cavity 320 of base member 300 and allow adhesive to set and cure |
| 7 | Cut pylon 500 to an appropriate length so that the artificial hand approximates the position of the person's anatomical hand |
| 8 | Insert one end of pylon 500 into cavity 360 of base member 300 |
| 9 | Insert the opposite end of pylon 500 into cavity 420 of coupling member 400 |
| 10 | Provide holes in the pylon by inserting a drill into hole 370 of base member 300 and hole 460 of coupling member 400 |
| 11 | Push bolts through holes 370 and 460 as well as through the holes that were drilled in the pylon |
| 12 | Secure the bolts by applying lock washer and nuts to the threaded ends of the bolts that extend out of the holes. |
| 13 | Provide pull cord 350 with a knot at one end and push the opposite end of the cord through guide hole 240 of palm member 200 and guide hole 340 of base member 300 with the cord having a length that can extend to the person's arm stump |

As noted herein, there are a number of alternative steps that can be followed to assemble the artificial hand from a kit of these components. Instead of applying adhesive to extension member 180 of palm member 100 or into cavity 320 of base member 300, extension member 180 can be secured to cavity 320 through the use of screws or by drilling a through hole and using a fastener arrangement of a bolt, lock washer and nut. And instead of drilling holes in the pylon, the pylon can be adhered to the cavities of the base and coupling members using a suitable adhesive. When bolts are used, additional washers can be provided to prevent the bolt head or lock washers from damaging the plastic members that they contact. Additionally, a metal sleeve and be applied to the doles to prevent contact of the bolting with the various plastic components that it passes through. The pull cord is an optional component although in most cases it is preferred.

In another variation, the attachment of the pylon to the base and coupling members can be deferred until the point in time when the artificial hand is to be attached to the person. This enables the hand to be prepared before seeing the person in need such that the length of the pylon can be determined once the person is available. Of course, if the hand is assembled when the person is present, the steps in Table 1 can be followed.

Table 2 is an illustrative flow chart for the method of attaching the artificial hand of the invention to a person in need thereof

TABLE 2

Attaching an artificial hand to a person in need thereof

| Number | Step details |
|---|---|
| 1 | Assemble the artificial hand according to the method of Table 1 |
| 2 | Apply a fabric or cloth sock onto the arm stump of the person |
| 3 | Apply a separator plastic bag or plastic film over the fabric or cloth sock |
| 4 | Providing a settable casting sock over the plastic bag or film |
| 5 | Activating the casting sock by immersion in water and applying the activated casting sock over the plastic film or bag |
| 6 | Allowing the casting sock to cure or set to a final rigid shape |
| 7 | Placing the base of the coupling member of the artificial hand adjacent the base of the rigid casting sock at the end of the person's arm stump and adhesively attaching the coupling member to the rigid casting sock with an epoxy or other adhesive |
| 8 | Attaching the coupling member to the person's stump covered by the cured casting sock by wrapping activated casting tape around the coupling member and solid casting sock |
| 9 | Allow the casting tape to set to form a hardened cast to complete the attachment |
| 10 | Applying an elastomeric material over the cured casting tape. |

Other features of the components that are typically attached to a person's stump are disclosed in the kits of U.S. Pat. No. 10,376,390 and U.S. patent application Ser. No. 16/538,751, the entire content of each of which is expressly incorporated herein by reference thereto. This includes the parts that are placed on the person before attaching the artificial hand thereto.

All of the necessary components described herein are typically provided in a box or other enclosure along with any other common components such as fasteners, adhesives, instructions, etc. so that the recipient of the box has all of the necessary parts and information to assemble the artificial hand and to attach it to a person in need thereof. The kit also typically includes bolts, nuts, lock washers and flat washers as needed for fastening components together. Also, appropriate adhesives, which generally are thermosetting adhesives, along with fiberglass reinforcement are also included in the kits.

It is to be understood that additional embodiments of the present invention described herein may be contemplated by one of ordinary skill in the art and that the scope of the present invention is not limited to the specific and preferred embodiments that are disclosed. While specific embodiments of the present invention have been illustrated and described, numerous modifications may come to mind to a skilled artisan without significantly departing from the true spirit and scope of the invention, and the protection provided herewith is limited only by the appended claims and equivalents thereof.

What is claimed is:

1. An artificial hand for a person in need thereof comprising:

first and second palm members, each containing at least one finger component, with the palm members connected together for rotation between a first, closed position wherein the finger components of the palm components are interspersed together and a second, open position wherein the finger components of the palm components are spaced apart to allow grasping of an object;

an alignment mechanism associated with the first and second palm members to guide rotation between the first and second positions, wherein the alignment mechanism comprises a tab member located on the first palm member and spaced sidewalls on the second palm member defining a slot therebetween, wherein the slot is configured and dimensioned to receive at least a portion of the tab member therein to facilitate rotation between the first and second positions, wherein the tab member of the first palm member includes a wall that is configured and dimensioned to contact a rear wall of the slot of the second palm member such that contact of these walls acts as a stop member for the first, closed position;

a fastener for connecting the first and second palm members together, wherein the fastener passes through the side walls and slot of the second palm member and through a lower portion of the tab member of the first palm member; and a biasing member operatively associated with the first and second palm members configured and arranged for urging the palm members towards the first, closed position, with the biasing member further configured and dimensioned to be stretched or elongated to allow the palm members and their respective finger components to move to the second, open position to receive an object and to secure the object between the finger components as the biasing member attempts to contract from being stretched or elongated.

2. The artificial hand of claim 1, wherein the at least one finger component of the first palm member includes one finger component a portion which is elongated and arcuate and the at least one finger component of the second palm member includes at least two finger components, each having a portion of which is elongated and arcuate, with the arcuate portions arranged on the respective finger components to face each other and define an opening therebetween when the palm members and finger components are in the second, open position.

3. The artificial hand of claim 2, wherein the one finger component of the first palm member is interdigitated between the two finger components of the second palm member.

4. The artificial hand of claim 2, wherein the finger components of the first and second palm members include pad members respectively located on the portions that are arcuate, distal portions of the finger components, or on both the arcuate portions and the distal portions of the finger components.

5. The artificial hand of claim 1, wherein the palm members are made of plastic and the fastener is a horizontal bolt that passes through the side walls and slot of the second palm component and through the lower portion of the tab member of the first palm member with the bolt secured by a nut.

6. The artificial hand of claim 1, wherein the first and second palm members include a groove or recess on an outer portion thereof to receive a portion of the biasing member therein, and the biasing member is a rubber cord or strap.

7. An artificial hand for a person in need thereof comprising:

first and second palm members, each containing at least one finger component, with the palm members connected together for rotation between a first, closed position wherein the finger components of the palm components are interspersed together and a second, open position wherein the finger components of the palm components are spaced apart to allow grasping of an object;

an alignment mechanism associated with the first and second palm members to guide rotation between the first and second positions, wherein the alignment mechanism comprises a tab member located on the first palm member and spaced sidewalls on the second palm member defining a slot therebetween, wherein the slot is configured and dimensioned to receive at least a portion of the tab member therein to facilitate rotation between the first and second positions;

a fastener for connecting the first and second palm members together, wherein the fastener passes through the side walls and slot of the second palm member and through a lower portion of the tab member of the first palm member;

a biasing member operatively associated with the first and second palm members configured and arranged for urging the palm members towards the first, closed position, with the biasing member further configured and dimensioned to be stretched or elongated to allow the palm members and their respective finger components to move to the second, open position to receive an object and to secure the object between the finger components as the biasing member attempts to contract from being stretched or elongated; and a base member that includes a first cavity at one end and a second cavity at the opposite end, wherein the first palm member includes a mounting extension extending below the tab member for placement into and securement to the first cavity of the base member.

8. The artificial hand of claim 7, further comprising a pylon having a first end which is received in and secured to the second cavity of the base member; wherein the pylon comprises a wooden dowel within a plastic tube.

9. The artificial hand of claim 8, further comprising a coupling member having a cylindrical body, a cavity for receiving and securing thereto a second end of the pylon, and a closed base.

10. The artificial hand of claim 7, further comprising a grasping member operatively associated with the second palm member for moving that palm member towards or to the second, open position.

11. The artificial hand of claim 10, wherein the grasping member comprises a pull cord, a first end of which is secured to the second palm member and a second end of which is associated with the base member.

12. The artificial hand of claim 11, wherein the base member and the second palm member or its respective finger component each include a guide hole, wherein the pull cord passes through each guide hole, the first end includes a knot to prevent the pull cord from passing back through the guide hole of the second palm member, and the second end passes through the guide hole of the base member for grasping.

13. The artificial hand of claim 7, further comprising:

a pylon having a first end which is received in and secured to the second cavity of the base member; wherein the pylon comprises a wooden dowel within a plastic tube; and a coupling member having a cylindrical body, a cavity for receiving and securing thereto a second end of the pylon, and a closed base.

14. The artificial hand of claim 7, wherein the at least one finger component of the first palm member includes one finger component a portion which is elongated and arcuate and the at least one finger component of the second palm member includes at least two finger components, each having a portion of which is elongated and arcuate, with the arcuate portions arranged on the respective finger components to face each other and define an opening therebetween when the palm members and finger components are in the second, open position.

15. A kit for preparing an artificial hand for a person having a missing hand and a remaining arm stump, the kit having a plurality of components, comprising:

first and second palm members, each containing at least one finger component, with the palm members connected together for rotation between a first, closed position wherein the finger components of the palm components are interspersed together and a second, open position wherein the finger components of the palm components are spaced apart to allow grasping of an object;

an alignment mechanism associated with the first and second palm members to guide rotation between the first and second positions, wherein the alignment mechanism comprises a tab member located on the first palm member and spaced sidewalls on the second palm member defining a slot therebetween, wherein the slot is configured and dimensioned to receive at least a portion of the tab member therein to facilitate rotation between the first and second positions;

a fastener for connecting the first and second palm members together, wherein the fastener passes through the side walls and slot of the second palm member and through a lower portion of the tab member of the first palm member;

a biasing member operatively associated with the first and second palm members configured and arranged for urging the palm members towards the first, closed position, with the biasing member further configured and dimensioned to be stretched or elongated to allow the palm members and their respective finger components to move to the second, open position to receive an object and to secure the object between the finger components as the biasing member attempts to contract from being stretched or elongated;

a base member that includes a first cavity at one end and a second cavity at the opposite end, wherein the first palm member includes a mounting extension extending below the tab member for placement into and securement to the first cavity of the base member;

a pylon having a first end which is received in and secured to the second cavity of the base member; wherein the pylon comprises a wooden dowel within a plastic tube; and a coupling member having a cylindrical body, a cavity for receiving and securing thereto a second end of the pylon, and a closed base.

16. The kit of claim 15, further comprising a grasping member operatively associated with the second palm member for moving that palm member towards or to the second, open position; wherein the grasping member comprises a pull cord, a first end of which is secured to the second palm member and a second end of which is associated with the base member; wherein the base member and the second palm member or its respective finger component each include a guide hole, and wherein the pull cord passes through each guide hole, the first end includes a knot to prevent the pull cord from passing back through the guide hole of the second palm member, and the second end passes through the guide hole of the base member.

17. The kit of claim 15, further comprising:

a flexible sheath adapted to fit on the person's stump;

a casting sock of a fabric containing a water activated settable material that, after activation, is adapted to fit over the flexible sheath; and casting tape of a fabric containing a water activated settable material and provided in one or more lengths that, after activation, are capable of attaching the coupling member to the person's arm stump while also covering the flexible sheath.

18. A method for preparing artificial hand for a person having a missing hand and a remaining arm stump, which method comprises:

providing the kit of components of claim 15; and assembling the artificial hand by connecting the alignment mechanism and palm members with the fastener, placing the biasing member about the palm members, inserting the first palm member into the base member, securing a first end of the pylon to the second cavity of the base member, and securing a second end of the pylon to the coupling member.

19. A method for preparing artificial hand for a person having a missing hand and a remaining arm stump, which method comprises:

providing the kit of components of claim 16; and assembling the artificial hand by connecting the alignment mechanism and palm members with the fastener, placing the biasing member about the palm members, inserting the first palm member into the base member, placing the pull cord through the guide holes of the first palm member and base member, securing a first end of the pylon to the second cavity of the base member, and securing a second end of the pylon to the coupling member.

20. A method for preparing artificial hand for a person having a missing hand and a remaining arm stump, which method comprises:

providing the kit of components of claim 17;

inserting the first palm member into the base member;

securing a first end of the pylon to the second cavity of the base member;

placing the flexible sheath on the person's arm stump;

providing the casting sock on the person's stump;

activating the casting sock by immersion in water and applying the activated casting sock over the flexible sheath;

allowing the casting sock to cure or set to a final rigid shape;

providing a socket support beneath the casting sock;

joining the socket support to the rigid shape of the casting sock with an adhesive that contacts a base of the casting sock below the end of the person's arm stump;

wrapping the socket support and rigid shape of the casting sock with the casting tape after the casting tape has been activated by immersion in water and allowing the wrapped casting tape to set and cure to a solid;

attaching the coupling member to the person's stump covered by the rigid shape of the casting sock by wrapping the activated casting tape around the coupling member while also covering the rigid shape of the casting sock;

cutting the pylon to an appropriate length so that the artificial hand is positioned to match that of the person's other hand; and attaching one end of the pylon to the cavity of the coupling member and the other end to the artificial hand.

* * * * *